US008609616B2

(12) United States Patent
Hansen et al.

(10) Patent No.: US 8,609,616 B2
(45) Date of Patent: Dec. 17, 2013

(54) STRONTIUM-CONTAINING COMPOUNDS FOR USE IN THE PREVENTION OR TREATMENT OF NECROTIC BONE CONDITIONS

(75) Inventors: Christian Hansen, Vedbaek (DK); Henrik Nilsson, Copenhagen K (DK); Stephan Christgau, Gentofte (DK); Henry G Bone, III, Grosse Point, MI (US)

(73) Assignee: Osteologix A/S, Copenhagen (DK)

( * ) Notice: Subject to any disclaimer, the term of this patent is extended or adjusted under 35 U.S.C. 154(b) by 6 days.

(21) Appl. No.: 13/182,798

(22) Filed: Jul. 14, 2011

(65) Prior Publication Data
US 2011/0269675 A1 Nov. 3, 2011

Related U.S. Application Data

(63) Continuation of application No. 10/590,892, filed as application No. PCT/DK2005/000140 on Feb. 28, 2005, now abandoned.

(60) Provisional application No. 60/548,529, filed on Feb. 26, 2004.

(30) Foreign Application Priority Data

Feb. 26, 2004 (DK) ................................. 2004 00313

(51) Int. Cl.
*A61P 19/08* (2006.01)
(52) U.S. Cl.
USPC .......................................... 514/16.7; 424/617
(58) Field of Classification Search
USPC .......................................... 424/617; 514/16.7
See application file for complete search history.

(56) References Cited

U.S. PATENT DOCUMENTS

| 3,478,073 | A |   | 11/1969 | Thore |
| 4,056,567 | A |   | 11/1977 | Lamberti et al. |
| 4,939,164 | A |   | 7/1990  | Wierzbicki et al. |
| 5,075,336 | A |   | 12/1991 | Czernecki et al. |
| 5,128,367 | A |   | 7/1992  | Wierzbicki et al. |
| 5,851,556 | A |   | 12/1998 | Breton et al. |
| 5,856,356 | A | * | 1/1999  | Tsouderos et al. ............ 514/492 |
| 7,589,235 | B2 |  | 9/2009  | Christgau et al. |
| 7,595,342 | B2 |  | 9/2009  | Hansen et al. |
| 2002/0018748 | A1 |  | 2/2002 | Satz et al. |
| 2003/0013651 | A1 | * | 1/2003 | Lam et al. ...................... 514/12 |
| 2004/0059134 | A1 |  | 3/2004 | Vaysse-Ludot et al. |
| 2004/0059135 | A1 |  | 3/2004 | Vaysse-Ludot et al. |
| 2004/0063972 | A1 |  | 4/2004 | Vayssc-Ludot et al. |
| 2005/0013877 | A1 |  | 1/2005 | Jellum et al. |
| 2005/0142211 | A1 |  | 6/2005 | Wenz |
| 2006/0216358 | A1 |  | 9/2006 | Hansen et al. |
| 2006/0275503 | A1 |  | 12/2006 | Hansen et al. |
| 2008/0167513 | A1 |  | 7/2008 | Hansen et al. |
| 2008/0221213 | A1 |  | 9/2008 | Christgau et al. |
| 2010/0048697 | A1 |  | 2/2010 | Hansen et al. |
| 2010/0143473 | A1 |  | 6/2010 | Hansen et al. |
| 2013/0071496 | A1 |  | 3/2013 | Hansen et al. |

FOREIGN PATENT DOCUMENTS

| DE | 102 25 420 | 12/2003 |
| EP | 0 381 445 | 8/1990 |
| EP | 390 456 A2 | 10/1990 |
| EP | 0 404 558 | 12/1990 |
| EP | 0 415 850 | 3/1991 |
| EP | B 0 415 850 | 3/1991 |
| EP | 0 737 471 A | 10/1996 |
| EP | 0 813 869 | 12/1997 |
| GB | 990 957 | 5/1965 |
| WO | WO 98/35657 | 8/1998 |
| WO | WO 99/34772 | 7/1999 |
| WO | WO/00/01692 | 1/2000 |
| WO | WO 02/062351 | 8/2002 |
| WO | WO 03/028742 | 4/2003 |
| WO | WO/03/043626 | 5/2003 |
| WO | WO 2004/084920 | 10/2004 |
| WO | WO 2004/098617 | 11/2004 |
| WO | WO 2004/098618 | 11/2004 |
| WO | WO 2004/098619 | 11/2004 |
| WO | WO 2005/049038 | 6/2005 |
| WO | WO 2005/082385 | 9/2005 |
| WO | WO 2005/123098 | 12/2005 |
| WO | WO 2005/123192 | 12/2005 |
| WO | WO 2005/123193 | 12/2005 |

OTHER PUBLICATIONS

Dahl et al., "Incorporation and Distribution of Strontium in Bone", Apr. 2001, Bone, vol. 28 No. 4, pp. 446-453.*
Weinstein et al., "Inhibition of Osteoblastogenesis and Promotion of Apoptosis of Osteoblasts and Osteocytes by Glucocrticoids", Jul. 1998, The Journal of Clinical Investigation, vol. 102 No. 2, pp. 274-282.*
Office Action issued on May 25, 2010 by the Examiner in U.S. Appl. No. 10/590,892 (US 2008/0167513).
Office Action issued on Feb. 16, 2011 by the Examiner in U.S. Appl. No. 10/590,892 (US 2008/0167513).
Ammann et al., "Strontium ranelate improves bone resistance by increasing bone mass and improving architecture in intact female rats," .1 Bone Miner Res Dec. 2004;19(12):2012-20.
Anderson ct al., "Solubility of various forms of strontium titanatc in lungs: in vitro and in vivo studies," Health Ph vs Jun. 1999;76(6):628-34.

(Continued)

Primary Examiner — Ali Soroush
(74) Attorney, Agent, or Firm — Foley & Lardner LLP

(57) ABSTRACT

A method for the treatment and/or prophylaxis of an osteonecrotic bone disease in a mammal in need thereof, such as, e.g., idiopathic or secondary osteonecrosis, avascular bone necrosis, glucocorticoid induced bone ischemia/osteonecrosis, Legg-Calve-Perthes disease and femoral head necrosis, the method comprising administering an effective dose of a strontium-containing compound (a) to the mammal. A method for the treatment and/or prophylaxis of an osteonecrotic bone disease, such as, e.g., idiopathic or secondary osteonecrosis, avascular bone necrosis, glucocorticoid induced bone ischemia/osteonecrosis and femoral head necrosis, in a mammal who is to be or is treated with a therapeutic agent (b) known to or suspected of inducing apoptosis and/or necrosis of bone cells, the method comprising administering a strontium-containing compound (a) in combination with (b).

29 Claims, No Drawings

(56) References Cited

OTHER PUBLICATIONS

Anderson et al., "Strontium retention as a function of age in the dog," Rad Res 1968;34:153-69.
Appleton, "Changes in the plasma electrolytes and metabolites of the rat following acute exposure to sodium fluoride and strontium chloride," Arch Oral Biol Apr. 1995;40(4):265-8.
Apostoaei, "Absorption of strontium from the gastrointestinal tract into plasma in healthy human adults," Health Phys Jul. 2002;83(1):56-65.
Ardissino et al., "No difference in intestinal strontium absorption after oral or IV calcitriol in children with secondary hyperparathyroidism. The European Study Group on Vitamin D in Children with Renal Failure," Kidney Int Sep. 2000;58(3):981-8.
Armbrecht et al., "Effect of I ,25-dihydroxyvitamin D3 on intestinal calcium absorption in strontium-fed rats," Arch Biochem Biophys Feb. 1979;192(2):466-73.
A S 11 RA FI et al., "Pre- and posteruptive effects of low doses of strotium on dental caries in the rat," Caries Res 1980;14(5):341-6.
Bader et al., "The effect of hydroxylamine, mercaptans, divalent metals and chelators on (Na+plus K+)-ATPase. A possible control mechanism," Biochim Biophys Acta Mar. 18, 1970; 198(3):583-93.
Barbara et al., "Normal matrix mineral zation induced by strontium ranelate in MC3T3-E1 osteogenic cells," Metabolism Apr. 2004;53(4):532-7.
Barry et al, "The hemodynamic effects of strontium chloride in the intact dog," Proc Soc Exp Biol Med Oct. 1972;141(I):52-8.
Barto et al., "Sensitive method for analysis of strontium in human and animal plasma by graphite furnace atomic absorption spectrophotometry," Clin Chem Aug. 1995;41(8 Pt 1): I 159-63.
Berger et al., "[On mechanism of strontium deposition in bone tissue]," Acta Histochem 1965 Dcc 24;22(5):298-308, (in German, w/ English Abstract).
Best et al., "Strontium ions induce production of thrornboxane B2 and secretion of 5-hydroxytryptamine in washed human platelets," Biochern Pharmacol Mar. 1981 I 5;30(6):635-7.
Bianchi et al., "No difference in intestinal strontium absorption after an oral or an intravenous 1,25(OH)2D3 bolus in normal subjects. For the European Study Group on Vitamin D in children with renal failure," J Bone Miner Res Oct. 1999;14(10):1789-95.
Blumsohn, "Stable strontium absorption as a measure of intestinal calcium absorption: comparison with the double-radiotracer calcium absorption test," Clin Sc 1994;87:363-8.
Boivin et al., "Effects of bisphosphonates on matrix mineralization," 1 Musculoskelet Neuronal Interact Dec. 2002;2(6):538-43.
Boivin et al., "Strontium distribution and interactions with bone mineral in monkcy iliac bone after strontium salt (S 12911) administration," J Bone Miner Res Sep. 1996;11(9):1302-11.
Brandi, "New perspectives in the prevention and treatment of glucocorticoid-induced osteoporis," Clin and Experimental Rheum 2000;18(5):874-8.
Briggman et al., "The crystal structures of calcium maluii.ite dihydrate and strontium malonate," Acta Cryst (1977);8333:1900-06.
Brown et al., "Is the calcium receptor a molecular target for the actions of strontium on bone?," Osteoporosis Int 2003;14(3):S25-34.
Buehler et al., "Strontium ranelate inhibits bone resorption while maintaining bonc formation in alveolar bone in monkeys (*Macaca fascicularis*)," Bone Aug. 2001;29(2):176-9.
Burguera et al., "Age amd sex-related calcium and strontium concentrations in different types of human bones," Trace Elements and Electrolytes 2002;19(3):143-51.
Burton et al., "Discrimination between strontium and calcium and their passage from diet to the bone of adult man," Nature Mar. 3, 1962;193:846-7.
Cabrera et al., "Strontium and bone," J Bone Miner Res May 1999; 14(5):661-8.
Canalis et al., "The divalent strontium salt S12911 enhances bone cell replication and bone formation in vitro," Bone Jun. 1996;18(6):517-23.

Carafoli, "In vivo effect of uncoupling agents on the incorporation of calcium and strontium into mitochondria and other subcellular fractions of rat liver," J Gen Physiol Aug. 1967;50(7):1849-64.
Christopffersen et al., "Effects of strontium ions on growth and dissolution of hydroxyapatite and on bone mineral detection," Bone Jan. 1997;20(I):47-54.
Cohn et al., "Kinetics of strontium and calcium skeletal metabolism in the rat," Riv Patol Nerv Ment Aug. 1966;87(4):79-83.
Cole et al., "The toxicity of strontium and calcium," J Pharmcol Exp Ther 1941;404(71):1-5.
Creger et al., "Strontium and bone development under conditions of suboptimal vitamin D," Calc. Tissue Res., 1971;8(1):83-6.
Dahl et al., "Incorporation and distribution of strontium in bone," Bone Apr. 2001;28(4):446-53.
Delannoy et al., "Long-term treatment with strontium ranelate increases vertebral bone mass without deleterious effect in mice," Metabolism Jul. 2002;51(7):906-1 1.
D'Haese et al., "Increased bone strontium levels in hcmodialysis patients with osteornalacia," Kidney Int Mar. 2000;57(3):1107-14.
D'Ilaese et al., "Measurement of strontium in serum, urine, bone, and sofl tissues by Zeeman atomic absorption spectrometry," Clin Ch ern Jan. 1997;43(1):121-8.
Doggrell, "Present and future pharmacothcrapy for osteoporosis," Drugs Today (Barc) Aug. 2003;39(8):633-57.
Eisenberg, " Effect of intravenous phosphate on serum strontium and calcium," N Engl J Med Apr. 16, 1970;282(16):889-92.
Eisenberg, "Effects of androgens, estrogens and corticoids on strontium kinetics in man," J Clin Endocrinol Metab May 1966;26(5):566-72.
Ferraro et al., "The effect of strontium chloride upon alveolar bone," J Pcriodontol Jun. 1980;51(6):345-7.
Foreman et al., "Proceedings: Activation of anaphylactic histamine release by calcium and strontium ions," Br J Pharmacol Feb. 1972;44(2):326P.
Fujita ct al., "Retention and excretion of strontium-85 in mice, rats and rabbits—extrapolation to long-term retention in hunians, " Ilcalth Phys Apr. 1965;11:271-8I.
Gastineau et al., "Metabolic studies of a patient with osteoporosis and diabetes rnellitus: effects of testosterone ciianiliate :Hid slrolitiu in laciate," Mayo Med Ventures Mar. 1960;35(2):105-11.
G.Liosi I ut. al., "Clastogenic activity of strontium chloride on bone marrow cells in vivo," Biol Trace Elern Res Apr. 1990,2.(11:51-6.
Gibbons ct al, "The passage of calcium and strontium across the gut of the anaesthetized goat," J Physiol Apr. 1972;222(2):397-406.
Gruden, "The effect of lactose and iron on strontium absorption," Experientia Sep. 15, 1984;40(9):941-2.
Grynpas et al., "Effects of low doses of strontium on bone quality and quantity in rats," Bone 1990;11(5):313-9.
Grynpas et al., "Strontium increases vertebral bone volume in rats at a low dose that does not induce detectable mineralization defect," Bone Mar. 1996; I 8(3):253-9.
Gusmano et al., "Evaluation of the parameters of strontium metabolism in the rat as a function of age," Radiat Res Mar. 1968;33(3):540-53.
Gu I 1Eridge et al., "Delayed strontium absorption in post-menopausal osteoporosis and osteomalacia," Clin Sci Apr. 1968;34(2):351-63.
Hahn, "Strontium is a potent and selective inhibitor of sensory irritation," Dermatol Surg Sep. 1999 ;25(9):689-94.
Harrison et al., "Bone metabolism in rats, studied with stable strontium," J Endocrinol Nov. 1960;21:191-6.
Harrison et al., "On the mechanism of skeletal fixation of strontium. Parts 1 and 11," Archives BioChem 1959;80:97-113.
Harrison et al., "The metabolism of strontium in man," Clin Sci (Lond) Nov. 1955;14(4):681-95.
Hendrix et al., "Competition between calcium, strontium, and magnesium for absorpt on in thc isolated rat intestine," Clin Chem Dec. 1963;12:734-44.
Hibbins, "Strontium and strontium compounds," Kirk-Othmer Encyclopedia of Chemical Technology, 4lb ed. 1997;22:947-55.
Houston et al., "The systemic treatment of bonc metastases," Clin Orthop Relat Res Mar. 1995;(312):95-I 04.

(56) References Cited

OTHER PUBLICATIONS

International Search Report of International Application No. PCT/DK2004/000326, mailed Feb. 23, 2005.
International Search Report of International Application No. PCT/DK2004/00327, mailed Feb. 14, 2005.
International Search Report of International Application No. PCT/DK2004/000328, mailed Feb. 4, 2005.
International Search Report of International Application No. PCT/DK2005/000710, mailed Feb. 7, 2006.
International Search Report of International Application No. PCT/DK2005/000140, mailed Jul. 26, 2005.
Johnson et al., "The exchangeability of calcium and strontium of bone in vitro," Calcif Tissue Res. 1970;6(2):103-12.
Kroes et al., "Short-term toxicity of strontium chloride in rats," Toxicology Feb. 1977;711):11-21.
Leeuwenkamp et al., "Human pharmacokinetics of orally administered strontium.," Calcif Tissue Int 1990 Sep;47(3):136-41.
Lloyd, "Relative binding of strontium arid calcium in protein and non-protein fractions of serum in the rabbit," Nature. Jan. 27, 1968;217(126):355-6.
Loeser et al., "A study of the toxicity of strontium and comparison with other cations employed in therapeutics," J Lab Clin Med 1930;15:35-41.
MacDonald et al., "The skeletal deposition of non-radioactive strontium," 1 Biol Chem Jan. 1951;188(1):137-43.
Maltby ct al., "Exchange of potassium and strontium in adult bone," Am J Physiol Apr. 1982;242(4):H705-12.
Marie P.J., "Effects of strontium on bone tissue and bone cells," Therapeutic L'ses of Trace Elements, edited by Neve et al., Plenum Press, NY, 1996 pp. 277-282.
Marie et al., "An uncoupling agent containing strontium prevents bone loss by depressing bone resorption and maintaining bone formation in estrogen-deficient rats," J Bone Miner Res May 1993;8(5):607-15.
Marie et al., "Effect of low doses of stable strontium on bone metabolism in rats," Miner Electrolyte Metab 1985;11(1):5-13.
Marie et al., "Histomorphornetry of bone changes in stable strontium therapy," Envron. Health 1985;19:193-208.
Marie et al., "Mechanisms of action and therapeutic potential of strontium in bone," Calcif Tissue Int Sep. 2001;69(3):121-9.
Marie et al., Short-term effects of fluoride and strontium on bone formation and resorption in the mouse, Metabolism. Jun. 1986;35(6):547-5 I.
Matsumoto, "Effect of strontium chloride on bone resorption induced by prostaglandin E2 in cultured bone," Arch Toxicol 1988;62f2-3):240-1.
McCaslln et al., "The effect of strontium lactate in the treatment of osteoporosis," Staff Meeting at the Mayo Clinic 1959;34(13):329-34.
Meunier et al., "Design and methodology of the phase 3 trials for the clinical development of strontium ranelate in the treatment of women with postmenopausal osteoporosis," Osteoporos Int. 2003;14 Suppl 3:S66-76.
Meunier et al., "Strontium ranelate: dose-dependent effects in established postrnenopausal vertebral osteoporosis—a 2-year randomized placebo controlled trial," J Clin Endocrinol Metab. May 2002;87(5):2060-6.
Meunier et al., "The effects of strontium ranelate on the risk of vertebral fracture in women with postmenopausal osteoporosis," N Engl 1 Med Jan. 29, 2004;350(5):459-68.
Morohashi et al., "Effects of strontium on calcium metabolism in rats. II. Strontium prevents the increased rate of bone turnover in ovariectomized rats" Jpn J Pharrnacol Jun. 1995;68(2):l53-9.
Moller et al., "The course in time of the strontium retention in man," Health Phys Apr. 1968; I4(4):285-92.
Newton et al., "Metabolism of Ca and Sr in late adult life," Health Phys Oct. 1990;59(4):433-42.
Nielsen et al., "Influence of strontium on bone mineral density and bone mineral content measurements by dual Xray absorptiornetry," J Clin Densitom 1999 Winter;2(4):37I-9.
Palmer et al., "Discrimination in intestinal absorption of strontium and calcium," Proc Soc Exp Biol Med Nov. 1961; 105:296-300.
Palmer et al., "Strontium-calcium interrelationships in the growing rat," Am J Physiol Sep. 1964;207:561-6.
Price et al., "Hydrothermal crystallisation and x-ray structure of anhydrous strontium oxalate," Polyhedron 1999;18:2499-2503.
Regenster et al., "Prevention of early postmenopausal bone loss by strontium ranelate: the randomized, two-year, double-masked, dose-ranging, placebo-controlled PREVOS trial," Osteoporos Int Dec. 2002; I 3(12):925-31.
Reginster et al., "Strontium ranclate phase 2 dose-ranging studies: PREVOS and STRATOS studies," Osteoporos Int 2003;14 Suppl 3:S56-65.
Reginster et al., "Strontium ranelate: a new paradigm in the treatment of osteoporosis," Drugs Today (Barc). Feb. 2003;39(2):89-101.
Reginster,"Strontium ranelatc in osteoporosis," Curr Pharm Des 2002;8(21):1907-16.
Reid et al., "The assessment of intestinal calcium absorption using stable strontium," Calcif Tissue Int. May 1986;38(5):303-5.
Schmidbaur et al., "Metal ion binding by amino acids: strontium and barium L-asspartate trijudrate SR/BA(L-ASP) 3h20," Chemische Berichte, Verlas Chemie GMBH 1990;123(8):I 599-602.
Schmidbaur et al., "Preparation and crystal structures of magnesium, strontium, and barium 1-glutamate hydrates," Chem Ber 1989;122:1433-8.
Schoenberg, "Extent of strontium substitution for calcium in hydroxyapatite," Biochim Biophys Acta. Jul. 23, 1963;75:96-103.
Schroeder et al., "Trace metals in man: strontium and barium," J Chronic Dis Sep. 1972;25(9):491-517.
Schrooten et al., "Strontium causes osteomalacia in chronic renal failure rats," Kidney Int Aug. 1998;54(2):448-56.
Shorr et al., "The usefulness of strontium as an adjuvant to calcium in the remineralization of the skeleton in man," Bull Hosp Joint Dis Apr. 1952;13(1):59-66.
Skoryna, "Effects of oral supplementation with stable strontium," Can Med Assoc J Oct. 1, 1981;125(7):703-I 2.
Sorbera et al., "Strontium ranelate treatment and prevention of osteoporosis bone resorption inhibitor bone formation stimulant," Drug Fut Apr. 2003;28(4):328-35.
Storey, "Calcium and strontium changes in bone associated with continuous administration of stable strontium to rats," Arch Biochem Biophys Mar. 20, 1968;124(0:575-81.
Storey, "Strontium 'rickets': bone, calcium and strontium changes," Australas Ann Med Aug. 1961;10:213-22.
Svensson et al., "The effect of strontium and manganese on freshly isolated chondrocytes," Acta Pathol Microbiol Immunol Scand [A] May 1985;93(3):115-20.
Ten Bolscher et al., "Strontium as a marker for intestinal calcium absorption: the stimulatory effect of calcitriol," Clin Chem 2000;46(2):248-51.
Uriu et al., "Uncoupling between bone formation and resorption in ovariectomized rats with chronic cadmium exposure," Toxicol Appl Pharmacol May 2000 I ;164(3):264-72.
Warren et al., "Metabolic balances of strontium in man," Clin Orthop Rclat Res Jun. 1976;(117):307-20.
Barlow, "Strontium and Osteoporosis," Journal of the British Menopause Society; Mar. 2003 March; 9(1) 7.
Robinson N.A. & Yeo J.F. "Bispho[honates—A word of caution," Ann. Acad Med. Singapore, 2004; 33 (4 Suppl):48-49.
Greenberg, M.S. "Intravenous bisphosphonates and osteonecrosis," Oral Surg. Oral Med Oral Pathol Oral Radiol Endod., 2004 vol. 98, • • 259-60.
Reginster, J.Y., "Stronium renaletein osteoporosis," Curr. Pharm. Des. 2002, vol. 8, pp. 1907-1916.
Astrand, J. and Asspenberg P, "Systemic alendronate prevents resorption of necrotic bone during revascularizaton. A bone chamber study in rats," BMC Musculoskelet Disord. 2002, vol. 3:19, pp. 1-5.
Brousse C., "Osteoarticular complications of corticotherapy," Hepato-Gastro, 2000 France, vol. 7(3), pp. 173-178.
"Depistage Isotopique de l'Osteonecrose," Nouvelle Presse Medicate, Press Medicate, Paris, Fr., vol. 2(9), p. 583, 1998.

(56) References Cited

OTHER PUBLICATIONS

Beers, Berkow (EDS): "The Merck manual of diagnosis and therapy," 17'h Edn, 1999, Merck Research Laboratories, pp. 453-454.

Soerdjbalie-Maikoe, Vidya et al., "Strontium-89 (Metastron) and the bisphosphonate olpadronate reduce the incidence of spinal cord compression in patients with hormone-refractory prostate cancer metastatic to the skeleton," European Journal of Nuclear Medicine and Molecular Imaging, vol. 29(4), pp. 494-498, 2002.

About.com: Orthopedics: What you need to know about Osteoporosis: http://orthopedics.about.com/od/osteoporosis.htm?p=1 (Nov. 22, 2010).

About.com: Rheumatoid Arthritis/Joint Conditions: What is Osteonecrosis? http://arthritis.about.com/b/2010/05/09/what-is-osteonecrosis.htm?p=1 (Nov. 22, 2010).

International Search Report issued on Nov. 3, 2006 in application No. PCT/DK2005/000401 (corresponding to US 7,595,342).

Intenational Search Report issued on Jan. 12, 2006 in application No. PCT/DK2005/000404 (corresponding to US 7,595,342).

* cited by examiner

STRONTIUM-CONTAINING COMPOUNDS FOR USE IN THE PREVENTION OR TREATMENT OF NECROTIC BONE CONDITIONS

RELATED APPLICATIONS

This application is a continuation of United States Application Ser. No. 10/590,892, filed on Oct. 1, 2007 now abandoned, which is a 371 of PCT/DK2005/000140, filed Feb. 28, 2005, which claims benefit of U.S. Provisional Application No. 60/548,529, filed Feb. 26, 2004, all of which are herein incorporated by reference in their entirety for all purposes.

FIELD OF THE INVENTION

The present invention relates to methods for the treatment and/or prophylaxis of necrotic bone conditions and pharmaceutical compositions for use in such treatments.

BACKGROUND OF THE INVENTION

Necrotic bone conditions, such as idiopathic or secondary osteonecrosis, avascular bone necrosis, glucocorticoid induced bone ischemia/osteonecrosis, Legg-Calve-Perthes disease and femoral head necrosis are severe debilitating conditions. These conditions can be associated with medical interventions such as high dose glucocorticoid therapy and various treatments for HIV/AIDS, or they can arise spontaneously in susceptible individuals or as a consequence of other diseases such as Cushing syndrome, Storage diseases (i.e. Gauchers disease), haemaglobinopathies (e.g. sickle cell disease), pancreatitis, dysbaric conditions or trauma (e.g. dislocation or fracture).

Osteonecrosis is characterized by distinct histopathological features apparent on radiographs or bone scans. Although diagnostic methods for its identification have improved in recent years with the introduction of new sensitive high resolution MRI and other imaging techniques, no effective therapeutic agents or medical interventions have yet been developed to prevent and/or treat this condition.

Several pathological situations can induce osteonecrotic conditions, but among the most common clinical situations are high dose glucocorticoid use and treatments with apoptosis inducing compounds, such as the high dose anti-retroviral treatments administered to HIV infected patients.

Although most skeletal sites can be affected by osteonecrosis, the condition is most commonly found in the bone of the femoral head underneath the articular surface of the hip joint. The medical intervention of choice remains orthopedic surgery, where the necrotic bone area and affected joint structures are removed and replaced with a suitable implant. In some patients with necrotic bone disease, such as juveniles or patients with severe medical conditions, it can be highly problematic to perform this type of orthopedic surgery, and thus there is an unmet medical need for new medical therapies for prophylaxis and/or treatment of necrotic bone disease.

SUMMARY OF THE INVENTION

Accordingly, the present invention relates to a method for the treatment and/or prophylaxis of an osteonecrotic bone disease in a mammal in need thereof, such as, e.g., idiopathic or secondary osteonecrosis, avascular bone necrosis, glucocorticoid induced bone ischemia/osteonecrosis, Legg-Calve-Perthes disease and femoral head necrosis, the method comprising administering an effective dose of a strontium-containing compound (a) to the mammal.

As described above, one of the common causes of osteonecrotic bone diseases is the treatment with therapeutic agents known to or suspected of inducing apoptosis and/or necrosis of bone cells, thereby leading to an osteonecrotic bone disease. Accordingly, the present invention also relates to a method for the treatment and/or prophylaxis of an osteonecrotic bone disease, such as, e.g., idiopathic or secondary osteonecrosis, avascular bone necrosis, glucocorticoid induced bone ischemia/osteonecrosis and femoral head necrosis, in a mammal who is to be or is treated with a therapeutic agent (b) known to or suspected of inducing apoptosis and/or necrosis of bone cells, the method comprising administering a strontium-containing compound (a) in combination with (b).

The invention also relates to pharmaceutical compositions for use in the treatment and/or prophylaxis of osteonecrotic bone conditions.

DETAILED DESCRIPTION OF THE INVENTION

Osteonecrosis is distinct from most other metabolic bone diseases, in that the pathophysiology of the disease involves a vascular element and a regulation of the skeletal metabolism, other than seen in e.g. osteoporosis. It has been reported that some osteoporosis therapies, such as, e.g., the administration of bisphosphonates, may in fact be associated with an increased risk of developing osteonecrosis (Robinson N A & Yeo J F. Ann Acad Med Singapore. 2004; 33 (4 Suppl):48-9; Greenberg, M S. Oral Surg Oral Med Oral Pathol Oral Radiol Endod. 2004; 98:259-60). Accordingly, it does not appear that all of the commonly used osteoporosis therapies may be useful in the treatment of osteonecrosis.

However, the present inventors have demonstrated a therapeutic efficacy of a non-radioactive strontium salt in a model of osteonecrosis, and accordingly, the administration of a non-radioactive strontium-containing compound may in fact represent a novel and important approach for the prophylaxis as well as the treatment of an osteonecrotic bone disease in a mammal in need thereof, such as, e.g., idiopathic or secondary osteonecrosis, avascular bone necrosis, glucocorticoid induced bone ischemia/osteonecrosis, Legg-Calve-Perthes disease and femoral head necrosis.

Previous studies have shown that various strontium compounds modulate bone loss in osteoporosis. In vitro studies have demonstrated that strontium has a direct stimulatory effect on pre-osteoblastic cell division and maturation, and a direct or matrix-mediated inhibition of osteoclast activity (Reginster, J Y, Curr Pharm Des 2002:8 (21):1907-16). In other words, in vitro data indicates that strontium both works as an anti-resorptive and an anabolic agent. Various salts of strontium are known from the prior art, such as, e.g., strontium lactate, strontium chloride and strontium ranelate (distrontium salt of 2-[N,N-di(carboxymethyl)amino]-3-cyano-4-carboxymethylthiophene-5-carboxylic acid) described in EP-B 0 415 850. Other known strontium salts are e.g., strontium tartrate, strontium lactate, strontium phosphate, strontium carbonate, strontium nitrate and strontium sulfate.

Bone consists of an organic matrix comprising predominantly collagen type I, and an inorganic phase comprising calcium phosphate and calcium carbonate. Bone matrix proteins are synthesized by the osteoblasts. Formation of the organic bone matrix in turn serves as a scaffold for precipitation of the inorganic calcium salts of the bone mineral matrix, and gives the bone its structural strength. Degradation of bone is almost exclusively mediated by the multinuclear osteoclasts, which secretes acids responsible for dissolving the inorganic bone matrix and enzymes responsible for degrading the proteins of the organic bone matrix.

Normally the processes of bone resorption and bone formation are tightly coupled. Thus when bone resorption is reduced e.g. by an anti-resorptive agent, such as a bisphosphonate, bone formation will also be reduced to an almost similar extent. Conversely, if bone formation is increased e.g. by an anabolic treatment such as the hormone PTH, osteoclast recruitment and activity will also be up regulated. Strontium is reported to have an ability to uncouple bone formation and resorption processes, thus resulting in a sustained net positive bone balance. This is due to the combined actions of the strontium ion to reduce bone resorption and to increase or stabilize bone formation.

According to observations by the present inventors, it may be contemplated, that the anabolic effect of strontium on bone are of particular relevance for treatment of osteonecrotic lesions, as this property enables strontium to promote in-growth of new mineralized bone into the necrotic lesions and thus leading to repair of the condition.

In addition to this beneficial effect of strontium, the present inventors have surprisingly found that the strontium ion has an anti-apoptotic effect on bone cells, which can protect the cells from conditions inducing apoptosis such as, e.g., high dose glucocorticoid treatment or systemic administration of pro-apoptotic drugs such as, e.g., some forms of anti-retroviral or anti-neoplastic treatment. As many of the necrotic bone conditions may be associated with apoptosis of osteocytes and/or osteoblasts, the administration of a compound, which has an anti-apoptotic effect, may be of therapeutic value in the treatment and/or prophylaxis of such conditions. Accordingly, for necrotic bone conditions induced by the administration of therapeutic agents as described above, the administration of strontium-containing compounds may have a dual effect in that they both prevent the apoptosis and/or necrosis of bone cells eventually leading to an osteonecrotic bone disease, and also promote in-growth of new bone in case necrotic bone lesions caused by the apoptosis/necrosis of bone cells have already occurred.

For mammals in the need of or already in treatment with a therapeutic agent known to or suspected to induce apoptosis and/or necrosis of bone cells, it may therefore be of great value to receive an effective amount of a strontium-containing compound (a) as part of the same treatment regimen as the administration of the therapeutic agent (b).

Accordingly, the present invention relates to a method for the treatment and/or prophylaxis of an osteonecrotic bone disease, such as, e.g., idiopathic or secondary osteonecrosis, avascular bone necrosis, glucocorticoid induced bone ischemia/osteonecrosis and femoral head necrosis, in a mammal who is to be or is treated with a therapeutic agent (b) known to or suspected of inducing apoptosis and/or necrosis of bone cells, the method comprising administering an effective dose of a strontium-containing compound (a) in combination with (b).

The present inventors have found that the administration of a strontium-containing compound (a) in combination with a therapeutic agent (b) has prophylactic and/or therapeutic value in that one or more of the following beneficial effects can be obtained:

i) reduction in the incidence or severity of the osteonecrotic bone disease, wherein the incidence or severity of the osteonecrotic bone disease is reduced by at least 5%, such as, e.g., at least 10%, at least 20%, at least 30%, at least 40% or at least 50% in patients treated with (a) and (b) in combination as compared to patients treated with (b) alone in the same dose as (b) in the combination treatment, and/or ii) reduction of frequency and/or magnitude of side-effects of (b), wherein side effects are being defined as any clinical relevant observation pertaining to the disease or condition in the patient, such as bone-pain, joint-pain, immobility, functional impairment, weight loss or bone mineral density (BMD) decrease, and wherein the frequency and/or magnitude of the side-effects is reduced by at least 5%, such as, e.g., at least 10%, at least 20%, at least 30%, at least 40% or at least 50% in patients treated with (a) and (b) in combination as compared to patients treated with (b) alone in the same dose as (b) in the combination treatment.

As mentioned above glucocorticoid in high doses is one of the therapeutic agents (b) known to induce osteonecrotic bone diseases by bone cell apoptosis. Glucocorticoids as well as other related steroid hormones are given in high doses to modulate immune-system responses in several clinical situations, such as organ or bone marrow transplant, inflammatory and/or autoimmune diseases and some chronic persistent inflammatory states. It has been estimated that the incidence of avascular necrosis of bone among bone marrow transplant recipients exceeds 8% by 5 years (Socie G et al. Br J Haemata 1994: 86(3): 824-628). Accordingly, the therapeutic agent (b) may be a glucocorticoid and/or another steroid hormone.

Examples of other therapeutic agents known to or suspected of having a role in inducing apoptosis/necrosis of bone cells, eventually leading to osteonecrotic bone diseases, are anti-retroviral compounds, such as, e.g., efavirenz (Sustiva®), zidovudine (Retrovir®), lamivodine (Epivir®), abacavir (Ziagen®), zalcitabine (Hivid®), didanosine (Videx®), stavudine (Zerit®), tenofovir disoproxil fumarate (Viread®), emtricitabine (Emtriva®), fosamprenavir (Lexiva®), nevirapine (Viramune®), delavirdine (Rescriptor®), capravirine, enfuvirtide (Fuzeon®), saquinavir (Invirase®, Fortovase®), ritonavir (Norvir®), indinavir (Crixivan®), tipranavir, amdoxovir, elvucitabine, atazanivir (Reyataz®), nelfinavir (Viracept®), amprenavir (Agenerase®), PRO-542, TMC-114, TMC-125, BMS-56190, DPC-0830.

Other pro-apoptotic treatments associated with osteonecrosis are cytostatic and neoplastic agents used for prevention and treatment of cancer.

Some of the therapeutic agents used in the treatment of osteoporosis are also known to induce osteonecrosis. One example of such classes of therapeutic agents is the bisphosphonates.

In a specific embodiment of the invention the strontium-containing compound (a) and the therapeutic agent (b) are administered as separate compositions. The administration of (a) and (b) may take place simultaneously or sequentially, dependent on the type of therapeutic agent (b), the treatment regimen of (b), the nature of the disease towards which (b) is administered and the impact of (b) on the bone cells of the mammal receiving (b).

In one situation the therapeutic agent (b) is known to induce apoptosis and/or necrosis of bone cells and is administered according to the normal treatment regimen of (b) for the specific disease towards which (b) is administered. In such a situation, the strontium-containing compound (a) may be administered before the administration of (b) or simultaneously with (b). In case (a) is administered before (b), the administration of (a) may e.g. take place several hours, days or weeks or more before the administration of (b).

In case of high dose glucocorticoid treatment for e.g. an autoimmune disease such as systemic lupus erythomatosus (SLE), administration of a strontium compound (a) may be started simultaneously with high dose glucocorticoid (b). In situations where glucocorticoid treatment can be anticipated in advance, such as e.g. in treatment for patients receiving a renal transplant, the strontium compound (a) may be administered in advance of the glucocorticoid (b), such as e.g. on month, two weeks or one week or more before.

In another situation, the therapeutic agent (b) is only suspected to induce apoptosis and/or necrosis of bone cells. In this situation, the administration of the strontium-containing compound may not be initiated until effects of (b) on bone cells can be demonstrated. Accordingly, in such a situation the administration of (a) may be initiated with a substantial time delay to the initiation of the administration of (b), such as, e.g. several days or weeks.

An example of this is osteonecrosis associated with anti-retroviral therapy (b) in HIV, where the length of treatment duration is a significant risk factor for osteonecrosis development; treatment with a strontium compound (a) may be initiated up to 5 years or more after treatment with the antiretroviral therapy (b) is started.

Even though the strontium-containing compound (a) and the therapeutic agent (b) are administered sequentially, e.g. within a time interval of several hours, days, weeks, months or even years, they are still considered to be part of the same treatment.

The administration of the strontium-containing compound (a) may take place one or more times daily, such as, e.g., from 2-5 times daily. The administration may also take place one or more times weekly, such as from 1 to 3 times weekly.

The strontium-containing compound (a) may be administered the same number of times per day or e.g. week as (b), or (a) may be administered less times per day or e.g. week than (b) or more times per day or e.g. week than (b), dependent on the total daily or weekly dose of (a) needed. Even though (a) and (b) are not administered the same number of times per day or e.g. week, they are still considered to be part of the same treatment.

The administration of the strontium-containing compound (a) may be by the enteral or parenteral route or by topical administration. In a specific embodiment of the invention the administration is by the oral route.

In a specific method according to the invention the strontium-containing compound (a) and the therapeutic agent (b) are administered as a single composition.

Irrespectively of the method used for treatment and/or prophylaxis of the osteonecrotic bone conditions, i.e. whether the strontium-containing compound is administered alone, or used in a combination treatment together with a therapeutic agent (b) as described above, the following applies:

The strontium-containing compound (a) may be selected from the group consisting of strontium salts of an organic or an inorganic acid, and the salts may be in hydrate, anhydrous, solvate, polymorphous, amorphous, crystalline, microcrystalline or polymeric form. In one embodiment of the invention only non-radioactive isotopes of strontium are used.

The inorganic acid for making strontium salts may be selected from the group consisting of boric acid, bromous acid, carbonic acid, chloric acid, diphosphoric acid, disulfuric acid, dithionic acid, dithionous acid, fulminic acid, hydrazoic acid, hydrobromic acid, hydrochloric acid, hydrofluoric acid, hydroiodic acid, hydrogen sulfide, hypophosphoric acid, hypophosphorous acid, iodic acid, iodous acid, metaboric acid, metaphosphoric acid, metaphosphorous acid, metasilicic acid, nitric acid, nitrous acid, orthophosphoric acid, orthophosphorous acid, orthosilicic acid, phosphoric acid, phosphinic acid, phosphonic acid, phosphorous acid, pyrophosphorous acid, selenic acid, sulfonic acid, sulfuric acid, sulfurous acid, thiocyanic acid and thiosulfuric acid.

The organic acid may be selected from the group consisting of acetic acid, $C_2H_6COOH$, $C_3H_7COOH$, $C_4H_9COOH$, $(COOH)_2$, $CH_2(COOH)_2$, $C_2H_4(COOH)_2$, $C_3H_6(COOH)_2$, $C_4H_8(COOH)_2$, $C_5H_{10}(COOH)_2$, fumaric acid, maleic acid, malonic acid, lactic acid, citric acid, tartaric acid, oxalic acid, ascorbic acid, benzoic acid, salicylic acid, pyruvic acid, L- and D-aspartic acid, phthalic acid, carbonic acid, formic acid, methanesulfonic acid, ethanesulfonic acid, camphoric acid, gluconic acid, L- and D-glutamic acid, trifluoroacetic acid, ranelic acid, 2,3,5,6-tetrabromobenzoic acid, 2,3,5,6-tetrachlorobenzoic acid, 2,3,6-tribromobenzoic acid, 2,3,6-trichlorobenzoic acid, 2,4-dichlorobenzoic acid, 2,4-dihydroxybenzoic acid, 2,6-dinitrobenzoic acid, 3,4-dimethoxybenzoic acid, abietic acid, acetoacetic acid, acetonedicarboxylic acid, aconitic acid, acrylic acid, adipic acid, alanine, alpha-ketoglutaric acid, anthranilic acid, benzilic acid, arachidic acid, arginine, aspartic acid, asparagine, azelaic acid, behenic acid, benzenesulfonic acid, beta-hydroxybutyric acid, brassidic acid, capric acid, chloroacrylic acid, cinnamic acid, citraconic acid, crotonic acid, cyclopentane-1,2-dicarboxylic acid, cyclopentanecarboxylic acid, cystathionine, ranelic acid, decanoic acid, erucic acid, ethylenediaminetetraacetic acid, fulvic acid, fumaric acid, gallic acid, glutaconic acid, glutamic acid, glutamine, glutaric acid, gulonic acid, glycine, heptanoic acid, hexanoic acid, histidine, humic acid, hydroxystearic acid, isoleucine, isophthalic acid, itaconic acid, lanthionine, lauric acid (dodecanoic acid), leucine, levulinic acid, linoleic acid (cis,cis-9,12-octadecadienoic acid), lysine, malic acid, m-chlorobenzoic acid, melissic acid, mesaconic acid, methacrylic acid, monochloroacetic acid, myristic acid, (tetradecanoic acid), nonanoic acid, norvaline, octanoic acid, oleic acid (cis-9-octadecenoic acid), ornithine, oxaloacetic acid, palmitic acid (hexadecanoic acid), p-aminobenzoic acid, p-chlorobenzoic acid, petroselic acid, phenylacetic acid, phenylalanine, p-hydroxybenzoic acid, pimelic acid, propiolic acid, propionic acid, proline, serine, p-tert-butylbenzoic acid, p-toluenesulfonic acid, threonine, tryptophan, tyrosine, pyruvic acid, sarcosine, sebacic acid, serine, sorbic acid, stearic acid (octadecanoic acid), suberic acid, succinic acid, terephthalic acid, tetrolic acid, threonine, thyronine, tricarballylic acid, trichloroacetic acid, trimellitic acid, trimesic acid, tyrosine, ulmic acid, valine and cylohexanecarboxylic acid.

All acids, which the United States Food and Drug Administration (FDA) has regarded as safe for use in compositions for oral intake, may be used in the present invention. In one embodiment of the invention the acid may be a monoprotic or a diprotic acid. In yet another embodiment of the invention, the acid may be an amino acid in either the L-form or D-form or any mixture thereof.

Specific examples of strontium salts for use according to the invention are strontium chloride, strontium chloride hexahydrate, strontium citrate, strontium malonate, strontium succinate, strontium fumarate, strontium ascorbate, strontium aspartate in either L and/or D-form, strontium glutamate in either L- and/or D-form, strontium alpha-ketoglutarate strontium pyruvate, strontium tartrate, strontium glutarate, strontium maleate, strontium methanesulfonate, strontium benzenesulfonate, strontium ranelate and mixtures thereof.

In a specific embodiment of the invention, the strontium salt is composed of a strontium ion complexed to a di-carboxylic organic acid. Such a salt may also be a salt of an amine or an amino acid or mixtures thereof. A strontium salt of a di-carboxylic acid may be selected so the di-carboxylic acid moiety of the composition has a higher dissolution constant to strontium ions compared to calcium ions under physiological conditions. Thus, the dissolved salt will provide a solution with preferential binding of free calcium ions which may provide an advantage for promoting intestinal absorption of the strontium ion and thus improving the therapeutic effect and/or reducing the required dose necessary to achieve the prophylactic and/or therapeutic effect in the osteonecrotic condition.

The daily dose of ionic strontium may be at least about 0.01 g, such as, e.g. at least about 0.025 g, at least about 0.050 g, at least about 0.075 g, at least about 0.1 g, at least about 0.2 g, at least about 0.3 g, at least about 0.4 g or at least about 0.5 g or from about 0.01 to about 2 g such as, e.g., from about 0.1 to about 2 g, from about 0.1 to about 1 g, from about 0.15 to about 0.5 g, from about 0.3 to about 2 g or from about 1 to about 2 g.

In the case that the strontium-containing compound is strontium malonate, it may be administered in a dose corresponding to from about 0.1 to about 10 g daily calculated as anhydrous salt. More specifically, the salt may be administered in a dose corresponding to from about 0.2 to about 8 g daily such as, e.g., from about 0.4 to about 5 g daily, from about 0.6 to about 3 g daily or from about 0.7 to about 2 g daily calculated as anhydrous salt.

In case another strontium salt is used, the person skilled in the art will be able to calculate the total daily doses of strontium salt dependent on the counter-ion and the desired daily dose of ionic strontium.

As mentioned above, the administration of the strontium-containing compound (a) may take place one or more times daily, such as from 2 to 5 times daily. The administration may take place one or more times weekly, such as from 1 to 3 times weekly.

The administration of (a) may be by the enteral or parenteral route or by topical administration. In a preferred embodiment, the administration is by the oral route.

The mammal to be treated in a method according to the invention may be a human or a domestic animal, such as, e.g., a cat, a dog, a horse, a cow or a sheep. In a preferred embodiment the subject to be treated is a human, such as, e.g. a human female or male adult, adolescent or child.

The mammal in need of treatment may be identified and/or monitored by imaging techniques such as, e.g., X-ray, ultrasound, magnetic resonance imaging of the skeletal site suspected to be at risk for osteonecrosis and/or by assessment of altered bone turnover by the use of specific biochemical markers of bone turnover.

The details and specifics described above applies mutatis mutandis to the following:

In addition to the methods described above, the invention also relates to the use of a strontium-containing compound (a) for the manufacture of a medicament for treating and/or preventing an osteonecrotic bone condition, such as, e.g. idiopathic or secondary osteonecrosis, avascular bone necrosis, glucocorticoid induced bone ischemia/osteonecrosis, Legg-Calve-Perthes disease and femoral head necrosis, in a mammal.

The invention also relates to the use of a strontium containing-compound (a) and a therapeutic agent (b) for the manufacture of a medicament for treating and/or preventing an osteonecrotic bone condition in a mammal, wherein (b) is known to or suspected of inducing apoptosis and/or necrosis of bone cells leading to an osteonecrotic bone condition.

The invention further relates to a pharmaceutical composition comprising a strontium-containing compound (a), and a therapeutic agent (b) that is known to or suspected of inducing apoptosis and/or necrosis of bone cells leading to an osteonecrotic bone condition, optionally together with one or more pharmaceutically acceptable excipients, i.e. a therapeutically inert substance or carrier.

The carrier may take a wide variety of forms depending on the desired dosage form and administration route.

The pharmaceutically acceptable excipients may be e.g. fillers, binders, disintegrants, diluents, glidants, solvents, emulsifying agents, suspending agents, stabilizers, enhancers, flavors, colors, pH adjusting agents, retarding agents, wetting agents, surface active agents, preservatives, antioxidants etc. Details can be found in pharmaceutical handbooks such as, e.g., Remington's Pharmaceutical Science or Pharmaceutical Excipient Handbook.

Above are mentioned specific examples of the amounts of compounds administered. However, it will be understood that the amount of the compounds actually administered will be determined by a physician in light of the relevant circumstances including the condition to be treated, the choice of compounds to be administered, the age, weight, and response of the individual patient, the severity of the patient's symptoms and the chosen route of administration. While the present compositions are preferably administered orally, the compounds may also be administered by any other suitable route.

The pharmaceutical composition according to the invention may be in the form of a solid, semi-solid or fluid composition. In one embodiment of the invention, the pharmaceutical composition may be in the form of a tablet. The tablet may be coated with a coating that enables release of at least part of the salt in the proximal part of the small intestine, such as e.g. the duodenum and/or the proximal jejunum, such as at least 50% w/w, at least 60% w/w, at least 65% w/w, at least 70% w/w, at least 80% w/w or at least 90% w/w of the total amount of the salt contained in the tablet.

In another embodiment of the invention a compound may be selected have complete or predominant solubility in the ventricle such as at least 50% w/w, at least 60% w/w, at least 65% w/w, at least 70% w/w, at least 80% w/w or at least 90% w/w of the total amount of the salt contained in the tablet.

The tablet may have a shape that makes it easy and convenient for a patient to swallow. The tablet may thus e.g. have a rounded or a rod-like shape without any sharp edges. Furthermore, the tablet may be designed to be divided in two or more parts.

A semi-solid form of the composition may be a paste, a gel or a hydrogel.

The fluid form of the composition may be a solution, an emulsion including nano-emulsions, a suspension, a dispersion, a liposomal composition, a spray, a mixture, a syrup or an elixir.

Other suitable dosages forms of the pharmaceutical compositions according to the invention may be capsules, sachets, troches, devices etc.

The pharmaceutical compositions may be prepared by any of the methods well known to a person skilled in pharmaceutical formulation.

The invention also relates to a kit comprising two or more components, the first component comprising a strontium-containing compound (a) and the second component comprising a therapeutic agent (b) that is known to or suspected of inducing apoptosis and/or necrosis of bone cells leading to an osteonecrotic bone condition.

In certain cases it may be beneficial to include one or more further active substances in a method, a pharmaceutical composition or a kit according to the invention. The one or more further active substances may have a therapeutic and/or prophylactic effect on an osteonecrotic bone disease, such as, e.g., osteonecrosis. The term "active substance having a therapeutic and/or prophylactic effect on an osteonecrotic bone disease" includes active substances that can attain a particular medical result, such as, e.g., reduce the incidence of osteonecrosis, reduce bone pain associated with the osteonecrotic lesion increase bone density and/or improve healing of bone or prevent the occurrence of fracture in a subject at risk of developing an osteonecrotic condition. Examples of such substances are bone anti-resorptive and/or anabolic agents. However, one or more active substances having other effects than those mentioned above may also be included in a method or a pharmaceutical composition of the invention. Such active substances could be e.g. pain relievers (analgesic agents), anti-inflammatory agents, anti-retroviral agents, anti-neoplastic agents, disease-modifying anti-rheumatic drugs, or other anti-rheumatic drugs.

Specific examples of active substances, which may be used in a method or a pharmaceutical composition according to the invention are calcium-alpha-ketoglutarate, calcium and/or salts thereof, vitamin D such as, e.g., vitamin D3 and/or functional equivalents of vitamin D3, glucagon-like peptide-2, glucagons-like peptide-2 releasing compositions, non-steroidal anti-inflammatory drugs, pain relieving agents tumor necrosis factor alpha (TNF-α) inhibitors, inhibitors of IL-15 release or function and inhibitors of IL-1 release or function.

The following examples intend to illustrate the invention without limiting it in any way.

EXAMPLES

Example 1

Effect of Strontium Malonate in an Animal Model of Osteonecrosis

The rationale for the study was to assess the ability of strontium to act as a therapeutic and bone growth promoting (i.e. pro-anabolic) agent in an animal model of osteonecrosis. In this model, a syngenic necrotic bone graft was implanted into the femur of a recipient rat. The necrotic graft was degraded, while ingrowth of new bone occurred. At termination of the experiment, the structural grafts was removed and analyzed by histology to quantify both the degradation of the necrotic graft as well as ingrowth of new bone. Concomitant treatment with anabolic and/or anti-resorptive agents may be given after the insertion of the necrotic graft, and the effect monitored after termination of the experiment. This rat model has previously been described (Astrand J, Aspenberg P. *BMC Musculoskelet Disord.* 2002; 3(1):19).

Methods and Materials

The compounds (active strontium test-article: Sr-malonate, 189.6 g/mol; Placebo substance, calcium malonate, 142.1 g/mol) was suspended in drinking water for the rats. The salts were prepared in a solution of 1.6 g/l, which is close to saturation (22-25° C.). Thus extensive stirring was required to completely dissolve the substances. A new batch of drinking water was prepared fresh every week for the duration of the experiment. When not in use the solution was stored at room temperature in a closed container. Preliminary experiments showed that the animals each drink between 60 and 90 ml/24 h resulting in approximate strontium dosing of 120 mg strontium malonate/day equal to 55.4 mg of ionic strontium.

The study was performed in 20 male Sprague-Dawley rats ca. weight 350 g (corresponding to an age of 9-10 weeks), Taconic M&B, Lille Skensved, Denmark. The animals were allowed 2 weeks acclimatization before initiation of the experiment and were accordingly approximately 12 weeks old at implantation of the necrotic bone graft (week 0).

The study consisted of 2 groups each of 10 rats. The rats were randomly allocated to the groups before the initiation of the study. As in previous studies with therapeutic interventions in this model of osteonecrosis (Astrand J, Aspenberg P. *BMC Musculoskelet Disord.* 2002; 3(1):19) the study lasted for 6 weeks. At week 0 they were subjected to an operation with insertion of a necrotic bone graft, with cancelous (trabecular) bone grafts derived from female Sprague Dawley rats. The bone graft were excised from the female rats after necropsy, and frozen at −80° C. to kill all cells within the bone graft. The graft was then placed into a titanium chamber placed in the tibia of the right hind leg, in operation at full anesthesia. Treatment with strontium malonate or control (calcium malonate) was initiated from week 0. Food and water containing the suspended test substance was administered ad libitum. The rats were euthanized after 6 weeks, and the titanium chambers containing the necrotic bone grafts were removed and processed for histological assessment.

After careful removal from the titanium chamber, the grafts were decalcified in 10% formic acid, 2% formaldehyde for 14 days. The decalcified skeletal tissue was embedded in paraffin and cut in 1 μm sections parallel to the long axis of the graft. Each section was subsequently stained with hematoxylin and eosin, and visually scored for appearance of degradation of the necrotic graft as well as ingrowth of new bone.

Results

All 20 animals completed the 6 week study period, and were available for histological analysis. The histological analysis showed that in all rats, soft tissue had invaded the grafts. New bone had formed a bone ingrowth frontier. The main parameter of analysis was the measurement of this ingrowth distance. The two groups of animals showed significant differences in the extent of ingrowth of new bone. The strontium malonate treated group had an average ingrowth of 3.43 (±1.35 (SD)) mm compared to an average ingrowth of 2.24 (±1.00) p=0.038. This shows that strontium malonate had a significant anabolic effect, and thus indicates the potential use of this compound in both prophylaxis and treatment of osteonecrosis.

The strontium malonate used in the Examples herein has been prepared as described below:

Preparation of Strontium Malonate Anhydrate by Synthesis at 100° C.

Initially, a suspension of malonic acid (white colored) was prepared by adding 100 mL of millipore water to 10.406 g (0.1 moles) of solid malonic acid (Fluke, MW 104.06 g/mole, CAS no. 141-82-2, lot. no. 449503/1, filling code 44903076) in a 250 mL beaker. To this suspension was added 26.571 g (0.1 moles) of solid strontium hydroxide (Sigma Aldrich, $Sr(OH)_2 *8H_2O$, MW 265.71, CAS no. 1311-10-0). Then, a magnetic stirring rod was added and the stifling and heating was started to the point of boiling of the suspension. The final suspension was also white colored and the stirring was sustained by maintaining a medium rotation rate of the stirring apparatus. In order to prevent carbon dioxide from entering the solution, the beaker was covered by a covering glass.

After some minutes of boiling and stirring, the solution clarified and all the solid material dissolved. The boiling was maintained, and additional water was added when required, as to replace the water lost by boiling. After three hours of boiling, the solution was filtered while boiling on a Bachner funnel. Very small amounts of impurities were left in the filter. The filtrate was subsequently allowed to cool to room temperature, which resulted in growth of fine-powdered crystals of strontium malonate. Precipitation of the final product progressed rapidly during filtration and the majority of the product was found in the filter (unheated). Only in rare instants, the precipitation progressed in the filtrate. The product was filtered and dried at 110° C. in an oven for ½ hour followed by drying 12 hours in a dessicator over silica orange. Before analysis by x-ray crystallography and by Flame Atomic Absorption Spectrometry (F-AAS), the salts were ground by a mortar to fine powder.

The total yield of strontium malonate was approximately 98% before recrystallisation, and the majority of impurities consisted of reminisces of the reagents and of strontium carbonate. The product was unambiguously identified as strontium malonate (anhydrous) by x-ray crystallography and comparing the data to results of the Cambridge Crystallographic Database.

In a further improvement of the synthesis, anhydrous strontium malonate was produced in 10 kg scale in a method according to the present invention indicative of the applicability of the method for larger scale synthesis. 15.80 kg $Sr(OH)_2*8H_2O$ was dissolved in 63.2 l purified water and heated to 95-100° C. 5.63 kg malonic acid was dissolved in 4.1 l purified water, filtered where after an additional 1.4 l of water was added and the solution heated to 95-100° C. The two solutions were mixed in a closed reaction vessel under an inert nitrogen atmosphere and stirred under reflux for 20 min. Subsequently the heating was stopped and the solution was allowed to cool to 40-50° C. over 2-4 hours while strontium malonate was allowed to precipitate. The precipitate was filtered and the salt washed with an additional 13.2 l of water, followed by drying to complete dryness at vacuum in a temperature of 70° C. 9.4 kg anhydrous highly pure strontium malonate was obtained as a uniform microcrystalline white powder, corresponding to a yield of 94%. The product was unambiguously identified as strontium malonate (anhydrous) by x-ray crystallography and comparing the data to results of the Cambridge Crystallographic Database.

Tablet for use in a method according to the invention may be prepared as follows:

Formulation of Strontium Malonate in Tablets.

Strontium malonate can be formulated for pharmaceutical use in convenient tablets for oral administration. The tablets should be prepared with microcrystalline strontium malonate manufactured as described above. For production of the tablets the following procedure can be followed, which will result in approximately 12000 tablets.

3600 g Strontium Malonate, prepared as described above is mixed with 180 g Avicel PH102 (microcrystalline cellulose) Ph. Eur. After blending 144 g Polyvidone A Ph. Eur. And 450 g Purified Water Ph. Eur. is added to the mixture.

The weight of the mixture is controlled (theoretical weight 3924 g). After completion of the mixing process, the granulate material is sieved through a net with a pore size of 1.2 mm and dried at 40° C. in trays in a suitable drying oven. To the granulate is added 23 g Colloidal Anhydrous Silica (Aerosil 200) Ph. Eur, 284 g Avicel PH102 (microcrystalline cellulose) Ph. Eur. and 23 g Magnesium Stearate Ph. Eur. Thorough mixing is performed, and the material is sieved through a net with a pore size of 0.7 mm. This material is loaded on a tablet pressing machine.

Nine mm white round tablets (ø9 mm) with no score line are manufactured, each containing the following ingredients:

| | |
|---|---|
| Strontium malonate | 300 mg |
| Microcrystalline Cellulose Ph. Eur. | 43.5 mg |
| Polyvidone Ph. Eur. | 12 mg |
| Colloidal anhydrous silica Ph. Eur. | 2.25 mg |
| Magnesium Stearate Ph. Eur. | 2.25 mg |

In Pharmaceutical use for administering a 1.2 g dose of strontium malonate 4 tablets can be administered to a subject in need thereof. It follows that a person skilled in the art, by employing a tablet pressing machine with larger press heads can produce larger tablets containing more of the listed ingredients but with the same relative abundance.

The invention claimed is:

1. A method for the treatment of an osteonecrotic bone disease in a mammal in need thereof, the method comprising administering to the mammal an amount of a strontium-containing compound effective to treat and/or prevent an osteonecrotic bone disease.

2. The method according to claim 1, wherein the effective amount of the strontium-containing compound comprises a daily dose of strontium of at least about 0.01 g.

3. The method according to claim 1, wherein the administration takes place one or more times daily.

4. The method according to claim 3, wherein the administration takes place from 2-5 times daily.

5. The method according to claim 1, wherein the administration is by an enteral or parenteral route or by topical administration.

6. The method according to claim 5, wherein the administration is by an oral route.

7. A method for the treatment of an osteonecrotic bone disease, in a mammal who is to be or is treated with a therapeutic agent known to or suspected of inducing apoptosis and/or necrosis of bone cells, the method comprising administering to the mammal an amount of a strontium-containing compound effective to treat and/or prevent an osteonecrotic bone disease in combination with the therapeutic agent.

8. The method according to claim 7, wherein the apoptosis and/or necrosis of bone cells lead to an osteonecrotic bone disease.

9. The method according to claim 7, wherein the administration of the strontium-containing compound and the therapeutic agent leads to at least one of the following:
   i) reduction in the incidence or severity of the osteonecrotic bone disease, wherein the incidence or severity of the osteonecrotic bone disease is reduced by at least 5% in patients treated with the strontium-containing compound and the therapeutic agent in combination as compared to patients treated with the therapeutic agent alone in the same dose as the therapeutic agent in the combination, or
   ii) reduction of frequency and/or magnitude of side-effects of the therapeutic agent, wherein side effects are being defined as any clinical relevant observation pertaining to the disease or condition in the patient, and wherein the frequency and/or magnitude of the side-effects is reduced by at least 5% in patients treated with the strontium-containing compound and the therapeutic agent in combination as compared to patients treated with the therapeutic agent alone in the same dose as the therapeutic agent in the combination.

10. The method according to claim 7, wherein the therapeutic agent is a glucocorticoid and/or another steroid hormone.

11. The method according to claim 7, wherein the therapeutic agent is an anti-retroviral compound.

12. The method according to claim 7, wherein the therapeutic agent is a bisphosphonate.

13. The method according to claim 7, wherein the amount of the strontium-containing compound comprises a daily dose of strontium of at least about 0.01 g.

14. The method according to claim 7, wherein the strontium-containing compound and the therapeutic agent are administered as a single composition.

15. The method according to claim 7, wherein the strontium-containing compound and the therapeutic agent are administered as separate compositions.

16. The method according to claim 7, wherein the administration of the strontium-containing compound and the therapeutic agent take place simultaneously or sequentially.

17. The method according to claim 1, wherein the strontium-containing compound is selected from the group consisting of strontium salts of an organic or an inorganic acid.

18. The method according to claim 17, wherein the salt is in hydrate, anhydrous, solvate, polymorphous, amorphous, crystalline, microcrystalline or polymeric form.

19. The method according to claim 1, wherein the strontium-containing compound is strontium chloride, strontium carbonate, strontium citrate, strontium malonate, strontium succinate, strontium fumarate, strontium ascorbate, strontium pyruvate, strontium L-glutamate, strontium D-glutamate, strontium L-aspartate, strontium D-aspartate, strontium alpha-ketoglutarate, strontium lactate, strontium tartrate, strontium glutarate, strontium maleate, strontium methanesulfonate, strontium benzenesulfonate, strontium ranelate or mixtures thereof.

20. The method according to claim 1, wherein the osteonecrotic bone disease is idiopathic or secondary osteonecrosis, avascular bone necrosis, glucocorticoid induced bone ischemia/osteonecrosis, Legg-Calve-Perthes disease or femoral head necrosis.

21. The method according to claim 7, wherein the osteonecrotic bone disease is idiopathic or secondary osteonecrosis, avascular bone necrosis, glucocorticoid induced bone ischemia/osteonecrosis or femoral head necrosis.

22. The method according to claim 9, wherein the side effects pertain to bone-pain, joint-pain, immobility, functional impairment, weight loss or bone mineral density (BMD) decrease.

23. The method according to claim 11, wherein the antiretroviral compound is efavirenz, zidovudine, lamivodine, abacavir, zal citabine, didanosine, stavudine, tenofovir disoproxil fumarate, emtricitabine, fosamprenavir, nevirapine, delavirdine, capravirine, enfuvirtide, saquinavir, ritonavir, indinavir, tipranavir, amdoxovir, elvucitabine, atazanivir, nelfinavir, amprenavir, PRO-542, TMC-114, TMC-125, BMS-56190, or DPC-0830.

24. The method of claim 1, wherein the strontium-containing compound comprises strontium malonate.

25. The method of claim 7, wherein the strontium-containing compound comprises strontium malonate.

26. The method according to claim 1, wherein the strontium-containing compound comprises strontium succinate.

27. The method according to claim 7, wherein the strontium-containing compound comprises strontium succinate.

28. The method according to claim 1, wherein the amount of the strontium-containing compound comprises a daily dose of strontium of about 0.01 g to about 2 g.

29. The method according to claim 7, wherein the amount of the strontium-containing compound comprises a daily dose of strontium of about 0.01 g to about 2 g.

* * * * *